United States Patent
Lalgudi et al.

(10) Patent No.: US 11,560,447 B2
(45) Date of Patent: Jan. 24, 2023

(54) FORMALDEHYDE FREE MICROSPHERES AND ENCAPSULATION

(71) Applicant: Battelle Memorial Institute, Columbus, OH (US)

(72) Inventors: Ramanathan S. Lalgudi, Columbus, OH (US); Robert J. Cain, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 264 days.

(21) Appl. No.: 16/636,514

(22) PCT Filed: Aug. 3, 2018

(86) PCT No.: PCT/US2018/045103
§ 371 (c)(1),
(2) Date: Feb. 4, 2020

(87) PCT Pub. No.: WO2019/028315
PCT Pub. Date: Feb. 7, 2019

(65) Prior Publication Data
US 2020/0255582 A1    Aug. 13, 2020

Related U.S. Application Data

(60) Provisional application No. 62/541,308, filed on Aug. 4, 2017.

(51) Int. Cl.
| | |
|---|---|
| C08G 18/62 | (2006.01) |
| B01J 13/14 | (2006.01) |
| C08F 2/38 | (2006.01) |
| C08F 220/18 | (2006.01) |
| C08G 18/18 | (2006.01) |
| C08G 18/22 | (2006.01) |
| C08G 18/73 | (2006.01) |
| C08G 18/75 | (2006.01) |
| C08G 18/76 | (2006.01) |
| C08G 59/50 | (2006.01) |
| C08K 5/37 | (2006.01) |

(52) U.S. Cl.
CPC .......... *C08G 18/6225* (2013.01); *B01J 13/14* (2013.01); *C08F 2/38* (2013.01); *C08F 220/18* (2013.01); *C08G 18/18* (2013.01); *C08G 18/222* (2013.01); *C08G 18/73* (2013.01); *C08G 18/755* (2013.01); *C08G 18/7621* (2013.01); *C08G 18/7671* (2013.01); *C08G 59/50* (2013.01); *C08K 5/37* (2013.01)

(58) Field of Classification Search
CPC .................................................. C08G 18/6225
See application file for complete search history.

(56) References Cited

U.S. PATENT DOCUMENTS

| | | | |
|---|---|---|---|
| 2002/0193507 A1* | 12/2002 | Reusmann | C08G 18/6254 524/589 |
| 2007/0155859 A1 | 7/2007 | Song et al. | |
| 2007/0220686 A1* | 9/2007 | Jeanne-Rose | C08G 18/6212 8/406 |
| 2008/0071056 A1* | 3/2008 | Borst | C08F 291/00 528/44 |
| 2009/0111934 A1 | 4/2009 | Yuan et al. | |
| 2009/0240004 A1 | 9/2009 | Maier et al. | |
| 2013/0305796 A1 | 11/2013 | Hudson et al. | |

FOREIGN PATENT DOCUMENTS

| | | | | |
|---|---|---|---|---|
| EP | 0565206 A2 | | 10/1993 | |
| JP | 2011063731 A | * | 3/2011 | ............ C08L 75/04 |
| WO | 2013026809 A1 | | 8/2012 | |

OTHER PUBLICATIONS

JP-2011063731-A_Mar. 2011_English Translation.*
International search report from PCT/US2018/045103, dated Jan. 15, 2019.
D. M A Segura, et al., "Chapter 3 Chemistry of polyurethane adhesives and sealants" in: "Adhesives and sealants: basic concepts and high tech bonding", Jan. 1, 2005 (Jan. 1, 2005), Elsevier, Amsterdam; NL, XPO55522282, ISBN: 978-0-08-0044554-0; vol. 1, pp. 101-162, DOI: 10.1016/S1874-5695 (02) 80004-5.

* cited by examiner

*Primary Examiner* — Michael L Leonard
(74) *Attorney, Agent, or Firm* — Greer, Burns & Crain, Ltd.

(57) ABSTRACT

Processes for producing polymer microcapsules using vicinal functional oligomers are also described. The vicinal functional oligomers can be made by polymerizing an acrylate monomer, a styrene monomer, or both in the presence of a chain transfer agent. The vicinal functional oligomers can be reacted with epichlorohydrin to form vicinal epoxies. The vicinal epoxies can be reacted with polyamines to form epoxy polymer microspheres. The vicinal epoxies can be reacted with carbon dioxide in the presence of a catalyst to form vicinal cyclic carbonates. The vicinal cyclic carbonates can be reacted with polyamines to form isocyanate-free polymer microspheres. Polymer microspheres made by the processes are also described.

9 Claims, No Drawings

FORMALDEHYDE FREE MICROSPHERES AND ENCAPSULATION

CROSS-REFERENCE TO RELATED APPLICATIONS

This application is a U.S. National Phase under 35 U.S.C. § 371 of International Application No. PCT/US2018/045103, filed Aug. 3, 2018 which claims the benefit of U.S. Provisional Application No. 62/541,308 which was filed Aug. 4, 2017, entitled Formaldehyde Free Microcapsules and Encapsulation, the contents of each of which are incorporated by reference in their entirety.

BACKGROUND OF THE INVENTION

Melamine-urea-formaldehyde (MUF) is the state of the art material in microencapsulation. However, formaldehyde is currently under environmental and legislative scrutiny as it is a carcinogen. The use of formaldehyde during the processing of the microcapsules and the continued release of formaldehyde during storage and use is a concern.

Microencapsulation is used in wide variety of applications, including, but not limited to, fabric softener, laundry detergent, all-purpose surface cleaner, personal care fragrances, controlled release of agricultural, and pharmaceutical active ingredients. Many consumer and industrial companies are seeking alternative materials to MUF.

Alternative approaches to MUF encapsulation typically involve either using scavengers during the curing of the microcapsules and/or in the final formulation of the microcapsules, or substitution of formaldehyde with other aldehydes in the production of amino resins.

DESCRIPTION OF THE INVENTION

Surfactants (also known as emulsifiers and stabilizers) are used to produce polymers directly in particulate form by stabilizing the microspheres during polymerization. Without the surfactant, the polymerization continues and aggregates are formed rather than microspheres. However, the presence of surfactants in the final polymer particulate often poses challenges to achieve the desired product performance and cost. Polymerizable surfactants can be used to mitigate the presence of residual surfactant in the final product.

One aspect of the present invention involves a new class of polymerizable surfactants which can be used to make MUF-free microspheres. These materials comprise vicinal functional oligomers. In one embodiment, the oligomer is the reaction product of an acrylate monomer, or a styrene monomer, or both and a chain transfer agent.

In some embodiments, the acrylate monomer comprises acrylic acid, methacrylic acid, methyl methacrylate, t-butyl methacrylate, butyl methacrylate, lauryl methacrylate, stearyl methacrylate, N,N'-dimethyl amino ethyl methacrylate, acetoacetoxy ethyl methacrylate, or combinations thereof.

In some embodiments, the chain transfer agent is thioglycerol.

Another aspect of the invention involves processes for producing polymer microcapsules using the new class of polymerizable surfactants. In one embodiments, the process comprises polymerizing an acrylate monomer, or a styrene monomer, or both in the presence of a chain transfer agent to form a vicinal functional oligomer; and reacting the vicinal functional oligomer with an isocyanate and a polyol to form polyurethane polymer microspheres.

In some embodiments, the acrylate monomer comprises acrylic acid, methacrylic acid, methyl methacrylate, t-butyl methacrylate, butyl methacrylate, lauryl methacrylate, stearyl methacrylate, N,N'-dimethyl amino ethyl methacrylate, acetoacetoxy ethyl methacrylate, or combinations thereof.

In some embodiments, the chain transfer agent is thioglycerol.

In some embodiments, the isocyanate comprises toluene diisocyanate, isophorone diisocyanate, hexamethylene diisocyanate, methylene bisphenyl isocyanate, or combinations thereof.

In some embodiments, the polyol comprises ethylene glycol, 1,4-butane diol, 1,6-hexane diol, 1,3,6-hexane triol, trimethylol propane, poly(tetramethylene) glycol, poly caprolactone diol, poly ethyleneglycol adipate, poly ethyleneglycol succinate, poly ethyleneglycol sebacate, poly ethyleneglycol itoconate, or combinations thereof.

In some embodiments, the vicinal functional oligomer is a polystearyl methacrylate vicinal diol, and the isocyanate is a polyisocyanate.

Another aspect of the invention involves processes for making vicinal functional oligomers and for producing polymer particulates using these vicinal functional oligomers.

In one embodiment, the process of making a vicinal epoxy comprises: polymerizing an acrylate monomer, or a styrene monomer, or both in the presence of a chain transfer agent to form a vicinal functional oligomer; and reacting the vicinal functional oligomer with epichlorohydrin to form the vicinal epoxy.

In some embodiments, the process further comprises reacting the vicinal epoxy with a polyamine to form epoxy polymer microspheres.

In some embodiments, the vicinal epoxy is reacted with carbon dioxide in presence of a catalyst to form a vicinal cyclic carbonate.

In some embodiments, the catalyst comprises tetrabutyl ammonium bromide, 8-hydroxy quinoline aluminum, 8-hydroxy quinoline iron, 8-hydroxy quinoline vanadium, or combinations thereof.

In some embodiments, the process further comprises reacting the vicinal cyclic carbonate with a polyamine to form isocyanate-free hydroxyl polyurethane polymer microspheres.

In some embodiments, the polyamine comprises ethylene diamine, 1,3-propane diamine, 1,4-butane diamine, triethylene tetraamine, tetraethylene pentamine, 1,6-hexamethylne diamine, isophorone diamine, polyethylene imine, or combinations thereof.

In some embodiments, reacting the vicinal cyclic carbonate with a polyamine comprises reacting the vicinal cyclic carbonate with the polyamine and a polyfunctional cyclic carbonate, and wherein the vicinal cyclic carbonate is a polystearyl methacrylate vicinal cyclic carbonate.

In some embodiments, the polymer microspheres are spherical and have a particle size between about 0.01 microns and about 500 microns.

In some embodiments, the polymer microspheres encapsulate a solid or liquid active ingredient.

In some embodiments, the active ingredient comprises, benzisothiazolinone, quaternary ammonium salts, epoxy oligomers, acrylic oligomers, isocyanate oligomers, or 2,4-dichlorophenoxyacetic acid, sulfentrazone, or combinations thereof.

Another aspect of the invention is polyurethane polymer microspheres. In one embodiment, the microspheres comprise the reaction product of a vicinal functional oligomer with an isocyanate and a polyol.

Another aspect of the invention is epoxy polymer microspheres. In one embodiment, the microspheres comprise the reaction product of a vicinal epoxy with a polyamine.

Another aspect of the invention is isocyanate-free polyurethane polymer microspheres. In one embodiment, the microspheres comprise the reaction product of a vicinal cyclic carbonate with a polyamine.

In some embodiments, the polymer microspheres can be used to encapsulate solid and liquid active ingredients such as, but not limited to, benzisothiazolinone (BBIT), quaternary ammonium salts, epoxy oligomers, acrylic oligomers, isocyanate oligomers, 2,4-dichlorophenoxyacetic acid (2,4-D), sulfentrazone, or combinations thereof for controlled release applications.

In some embodiments, the polymer microspheres are mixed with polymeric binders to formulate coatings.

The processes for making microcapsules using the polymerizable surfactants include emulsion and reverse emulsion polymerization, suspension polymerization, and dispersion polymerization. Emulsion polymerization typically involves an aqueous medium, while reverse emulsion polymerization involves a non-aqueous medium. Suspension polymerization and dispersion polymerization can involve either an aqueous or non-aqueous medium.

When the microcapsules are used to encapsulate active ingredients, solid particles are typically encapsulated using suspension polymerization. Liquid particles are typically encapsulated using suspension polymerization, although dispersion polymerization can also be used. If the liquid active agents are soluble in water, they are typically encapsulated using reverse emulsion polymerization. If the liquid active agents are insoluble in water, they are typically encapsulated using emulsion polymerization.

The microcapsules can include stimuli-responsive functional groups attached to the polymers comprising the microcapsules. The functional groups enable the microcapsules to change in response to physical, chemical or biological stimuli in the local environment, such as change in pH, temperature, light, water or enzymes The microcapsules typically have a particle size in the range of about 0.01 micron to about 500 microns, or about 0.01 micron to about 400 microns, or about 0.01 micron to about 300 microns, or about 0.01 micron to about 200 microns, or about 0.01 micron to about 100 microns, or about 0.1 micron to about 80 microns, or about 0.1 micron to about 60 microns, or about 0.1 micron to about 50 microns, or about 0.1 micron to about 40 microns, or about 0.1 micron to about 30 microns, or about 0.1 micron to about 20 microns.

The vicinal functional oligomers are made from vicinal diols. The vicinal oligomers can be used to form polyurethane (PU) microspheres, hydroxyl polyurethane (HPU) microspheres, and microspheres made from other derivatives, such as epoxy microspheres.

The polymer microspheres typically have a particle size between 0.01 microns and 100 microns.

The vicinal functional oligomer can be produced by polymerizing an acrylate monomer and/or a styrene monomer in the presence of a chain transfer agent. Suitable acrylates include, but are not limited to acrylic acid, methacrylic acid, methyl methacrylate, t-butyl methacrylate, butyl methacrylate, lauryl methacrylate, stearyl methacrylate, N,N'-dimethyl amino ethyl methacrylate, acetoacetoxy ethyl methacrylate, or combinations thereof.

The chain transfer agent is typically thioglycerol.

The vicinal functional oligomer formed by the reaction of an acrylate and thioglycerol as the chain transfer agent is a vicinal diol. The vicinal diol can be reacted with isocyanates and a polyol to form PU microspheres. When isocyanate and polyol are reacted without the vicinal diol present, PU is formed, but not PU microspheres. Suitable isocyanates include, but are not limited to, toluene diisocyanate, isophorone diisocyanate, hexamethylene diisocyanate, methylene bisphenyl isocyanate, or combinations thereof. Suitable polyols include, but are not limited to, ethylene glycol, 1,4-butane diol, 1,6-hexane diol, 1,3,6-hexane triol, trimethylol propane, poly(tetramethylene) glycol, poly caprolactone diol, poly ethyleneglycol adipate, poly ethyleneglycol succinate, poly ethyleneglycol sebacate cafe, poly ethyleneglycol itoconate, or combinations thereof.

In one embodiment, the PU microspheres are the reaction product of polystearyl methacrylate vicinal diol, polyol, and polyisocyanate.

The vicinal diol can be reacted with epichlorohydrin to form a vicinal epoxy. The vicinal epoxy can then be reacted with a polyamine to form epoxy microspheres. Suitable polyamines include, but are not limited to, ethylene diamine, 1,3-propane diamine, 1,4-butane diamine, triethylene tetraamine, tetraethylene pentaamine, 1,6-hexamethylene diamine, isophorone diamine, polyethylene imine, or combinations thereof.

In another embodiment, the vicinal epoxy is reacted with carbon dioxide in presence of a catalyst to form vicinal cyclic carbonates. Suitable catalysts include, but are not limited to, tetrabutyl ammonium bromide, 8-hydroxy quinoline aluminum, 8-hydroxy quinoline iron, 8-hydroxy quinoline vanadium, or combinations thereof. The vicinal cyclic carbonates can be reacted with a polyamine to form HPU. Suitable polyamines include, but are not limited to, ethylene diamine, 1,3-propane diamine, 1,4-butane diamine, triethylene tetramine, tetraethylene pentaamine, 1,6-hexamethylene diamine, isophorone diamine, polyethylene imine, or combinations thereof.

One embodiment, the HPU microspheres are the reaction product of polystearyl methacrylate vicinal cyclic carbonate, polyfunctional cyclic carbonate, and polyamines.

EXAMPLES

A: Examples of Making Vicinal Functional Diol

Example 1A: Synthesis of Poly(Stearyl Methacrylate) (PSMA) Thioglycerol (TG)-1

In a 100 ml round bottom flask fitted with an overhead stirrer, a thermocouple, a condenser, and a dry gas inlet, 25 g stearyl methacrylate, 3.5 g of thioglycerol, 0.2 g azobisisobutyronitrile, (AIBN), and 28.7 g of toluene were added. The contents were heated to 60° C. for 16 hours under argon atmosphere. The contents were cooled to room temperature, and the product was isolated by removing the solvent using a Buchi laboratory rotary evaporator. The number average molecular weight was characterized by using GPC. The analysis was performed using tetrahydrofuran (THF) as the solvent, a 1 ml/min flow rate, and a testing time of 60 minutes. The chromatogram had three peaks corresponding to molecular weights of 3246, 1096, and 574.

Example 2A: Synthesis of PSMA TG-2

In a 100 ml round bottom flask fitted with an overhead stirrer, a thermocouple, a condenser, and a dry gas inlet, 25 g stearyl methacrylate, 1.4 g of thioglyceryl, 0.2 g AIBN, and 26.6 g of toluene were charged. The contents were heated to 60° C. for 16 hours under argon atmosphere. The contents were cooled to room temperature, and the product was isolated by removing the solvent using a Buchi laboratory rotary evaporator. The molecular weight was characterized by using GPC. The analysis was performed using THF as the solvent, 1 ml/min flow rate, and a testing time of 60 minutes. The chromatogram had three peaks corresponding to molecular weights of 4125, 1039, and 635.

Example 3A: Synthesis of PSMA TG-3

In a 100 ml round bottom flask fitted with an overhead stirrer, a thermocouple, a condenser, and a dry gas inlet, 25 g stearyl methacrylate, 0.7 g of thioglyceryl, 0.2 g AIBN, and 25.9 g of toluene were added. The contents were heated to 60° C. for 16 hours under argon atmosphere. The contents were cooled to room temperature, and the product was isolated by removing the solvent using a Buchi laboratory rotary evaporator. The molecular weight was characterized by using GPC. The analysis was performed using THF as the solvent, 1 ml/min flow rate, and a testing time of 60 minutes. The chromatogram had one peak corresponding to a molecular weight of 6372.

Example 4A: Synthesis of PSMA TG-4

In a 100 ml round bottom flask fitted with an overhead stirrer, a thermocouple, a condenser, and a dry gas inlet, 25 g stearyl methacrylate, 0.35 g of thioglyceryl, 0.2 g AIBN, and 25.55 g of toluene were charged. The contents were heated to 60° C. for 16 hours under argon atmosphere. The contents were cooled to room temperature, and the product was isolated by removing the solvent using a Buchi laboratory rotary evaporator. The molecular weight was characterized by using GPC. The analysis was performed using THF as the solvent, 1 ml/min flow rate, and a testing time of 60 minutes. The chromatogram had one peak corresponding to a molecular weight of 13,086.

Example 5A: Synthesis of Poly(laurylmethacrylate) (PLMA) TG

In a 100 ml round bottom flask fitted with an overhead stirrer, a thermocouple, a condenser, and a dry gas inlet, 25 g lauryl methacrylate, 0.7 g of thioglyceryl, 0.2 g AIBN, and 25.9 g of toluene were added. The contents were heated to 60° C. for 16 hours under argon atmosphere. The contents were cooled to room temperature, and the product was isolated by removing the solvent using a Buchi laboratory rotary evaporator. The molecular weight was characterized by using GPC. The analysis was performed using THF as the solvent, a 1 ml/min flow rate, and a testing time of 60 minutes. The chromatogram had one peak corresponding to a molecular weight of 5865.

Example 6A: Synthesis of Poly Dimethyl Amino Ethyl Methacrylate (NN-DMAEA) TG

In a 100 ml round bottom flask fitted with an overhead stirrer, a thermocouple, a condenser, and a dry gas inlet, 99.63 g 2-dimethyl amino ethyl methacrylate (NN-DMAEA), 0.11 g of thioglyceryl, 0.21 g AIBN, and 99.3 g of methyl ethyl ketone were added. The contents were heated to 60° C. for 16 hours under argon atmosphere. The contents were cooled to room temperature, and the product was isolated by removing the solvent using a Buchi laboratory rotary evaporator.

Example 7A: Synthesis of Poly Glycidyl Methacrylate TG

In a 250 ml round bottom flask fitted with an overhead stirrer, a thermocouple, a condenser, and a dry inert gas inlet, 50.02 g 2-glycidyl methacrylate, 6.82 g of thioglyceryl, 0.52 g AIBN, and 64.00 g of methyl ethyl ketone were charged. The contents were heated to 60° C. for 16 hours under argon atmosphere. The contents were cooled to room temperature as a clear colorless liquid.

B: Examples of Making Vicinal Functional Epoxides

Example 1B: Synthesis of PSMA Epoxide

To a 250 ml 3 neck flask equipped with an overhead stirrer, a thermocouple, a condenser, and a gas inlet, 60 g of 5,000 molecular weight PSMA-TG (example 3A), 2.22 g sodium hydroxide (NaOH), 0.54 g (tetrabutyl ammonium bromide, TBAB) and 4.44 g of epichlorohydrin. The contents were heated to 60° C. under argon and allowed to react overnight. The following day, the contents were cooled, and 64.44 g of toluene was added. The mixture was centrifuged at 3000 rpm for 15 minutes to remove any excess NaOH and sodium chloride byproduct.

C: Examples of Making Vicinal Functional Cyclic Carbonates

Example 1C: Synthesis of PSMA Cyclic Carbonate

The supernatant from example 1B and an additional 1.52 g of TBAB were charged into a 250 ml flask 3 neck flask equipped with an overhead stirrer, a thermocouple, a condenser, and a gas inlet. The flask contents were heated to 60° C., and then $CO_2$ was bubbled through the material using a fritted gas sparge tube. The reaction was held at 60° C. until the entire amount of epoxy was converted to carbonate. The product was confirmed by $H^1$ NMR (in $CDCl_3$) with the disappearance of the epoxy peaks at 2.7, 2.9, and 3.2 ppm.

D: Examples of Making Vicinal Functional Acetyl Acetonate

When t-butyl acetoacetonate is allowed to react with Vicinal functional oligomers obtained from examples from 1A to 7A and heated in 100 ml 3 neck flask equipped with a magnetic stirrer, a thermocouple, a glass fritted inlet, and a gas outlet bubbler, Vicinal functional acetyl acetonate will be produced.

E: Examples of Making Polyurethane (PU) Microspheres

Example 1E: Preparation of PU Microspheres Using Vicinal Functional Diol Obtained from Example 1A In a 250 ml 3-neck flask equipped with a thermocouple, a dry air inlet, a condenser, and a mechanical stirrer, 2.74 g soybean oil based polyol (Cargill X-210), 6.45 g ethylene glycol, 7.3 g PSMA TG-1, 85.28 g mineral oil, and 0.04 g dibutyl tin dilaurate (DBTDL) were added. The reaction contents were heated to 60° C. Once the reaction was at 60° C., 21.3 g of (Toluene diisocyanate, TDI) was added with an addition funnel. Once all the TDI was added, the contents were held at 60° C. overnight. The reaction is complete when the isocyanate peak in the IR has disappeared (~2250 cm$^{-1}$). After the reaction was complete, the contents were washed with petroleum ether or hexane to remove the mineral oil. The contents were filtered, and the solid was dried at room temperature.

Example 2E: Preparation of PU Microspheres Using Vicinal Functional Diol Obtained from Example 2A In a 250 ml 3-neck flask equipped with a thermocouple, a dry air inlet, a condenser, and a mechanical stir, 2.76 g (Cargill X-210), 6.46 g ethylene glycol, 7.34 g PSMA-TG-2, 85.23 g mineral oil, and 0.04 g DBTDL were charged. The reaction contents were heated to 60° C. Once the reaction was at 60° C., 20.5 g of TDI was added with an addition funnel. Once all the TDI was added, the contents were held at 60° C. overnight. The reaction is complete when the isocyanate peak in the IR has disappeared (~2250 cm$^{-1}$). After the reaction was complete, the contents were washed with hexane to remove the mineral oil. The contents were filtered, and the solid was dried at room temperature.

Example 3E: Preparation of PU Microspheres Using Vicinal Functional Diol Obtained from Example 3A In a 250 ml 3-neck flask equipped with a thermocouple, a dry air inlet, a condenser, and a mechanical stir, 2.7 g (Cargill X-210), 6.5 g ethylene glycol, 7.3 g PSMA-3, 85.2 g mineral oil, and 0.04 g DBTDL were charged. The reaction contents were heated to 60° C. Once the reaction was at 60° C., 20.0 g of TDI was charged with an addition funnel. Once all the TDI was added, the contents were held at 60° C. overnight. The reaction is complete when the isocyanate peak in the IR has disappeared (~2250 cm$^{-1}$). After the reaction was complete, the contents were washed with petroleum ether or hexane to remove the mineral oil. The contents were filtered, and the solid was dried at room temperature.

Example 4E: Preparation of PU Microspheres Using Vicinal Functional Diol Obtained from Example 4A In a 250 ml 3-neck flask equipped with a thermocouple, a dry air inlet, a condenser, and a mechanical stir, 2.72 g (Cargill X-210), 6.45 g ethylene glycol, 7.32 g PSMA-TG-4, 85.22 g mineral oil, and 0.04 g DBTDL were charged. The reaction contents were heated to 60° C. Once the reaction was at 60° C., 20.0 g of TDI was added with an addition funnel. Once all the TDI was added, the contents were held at 60° C. overnight. The reaction is complete when the isocyanate peak in the IR has disappeared (~2250 cm$^{-1}$). After the reaction was complete, the contents were washed with petroleum ether or hexane to remove the mineral oil. The contents were filtered, and the solid was dried at room temperature.

F: Examples of Making Poly Epoxide Microspheres

Example 1F: Preparation of Polyepoxide Microspheres Using Vicinal Functional Epoxides Obtained from Example 1B 10-75 parts bisphenol A diglycidyl ether, 25-90 parts amine (Ancamine® 2739), and 1-25 parts vicinal functional epoxides obtained from Example 1B, 0.1-5 parts DMP-30 were mixed in 100-300 parts mineral oil, and 10-100 parts toluene in a reaction vessel, and allowed to react in the temperature range between 10° C. to 200° C. to produce polyepoxide microspheres.

G: Examples of Making Poly Hydroxyl Urethane Microspheres 10-75 parts of cyclic carbonate derived from bisphenol A diglycidyl ether, 25-90 parts amine (Ancamine® 2739) and 1-25 parts vicinal functional cyclic carbonates obtained from Example 2C, 0.1-5 parts 1,8-Diazabicyclo[5.4.0]undec-7-ene (DBU) were mixed in 100-300 parts mineral oil, and 10-100 parts toluene in a reaction vessel, and allowed to react in the temperature range between 10° C. to 200° C. to produce poly hydroxyl urethane microspheres.

H: Examples of Making Polyamide Microspheres 10-75 parts of diisocyanates such as toluene diisocyanate, isophone diisocyanate, hexamethylene diisocyanate and the like, 25-90 parts acetoacetylated polyols, such as ethylene glycol, propylene glycol, butane diol, poly ethylene glycol and the like, and 1-25 parts vicinal functional acetyl acetonate from example D are mixed in 100-300 parts mineral oil, and 10-100 parts toluene in a reaction vessel, and allowed to react in the temperature range between 10° C. to 200° C. to produce poly amide microspheres.

By about, we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A process of making polyurethane microspheres consisting essentially of:
   polymerizing a monomer selected from the group consisting of an acrylate monomer, or a styrene monomer, or both, and thioglycerol to form a vicinal functional diol; and
   reacting reactants selected from the group consisting of the vicinal functional diol, an isocyanate, and a polyol to form polyurethane polymer microspheres.

2. The process of claim 1 wherein the acrylate monomer comprises acrylic acid, methacrylic acid, methyl methacrylate, t-butyl methacrylate, butyl methacrylate, lauryl methacrylate, stearyl methacrylate, N,N'-dimethyl amino ethyl methacrylate, acetoacetoxy ethyl methacrylate, or combinations thereof.

3. The process of claim 1 wherein the isocyanate comprises toluene diisocyanate, isophorone diisocyanate, hexamethylene diisocyanate, methylene bisphenyl isocyanate, or combinations thereof.

4. The process of claim 1 wherein the polyol comprises ethylene glycol, 1,4-butane diol, 1,6-hexane diol, 1,3,6- hexane triol, trimethylol propane, poly(tetramethylene) glycol, poly caprolactone diol, poly ethyleneglycol adipate, poly ethyleneglycol succinate, poly ethyleneglycol sebacate, poly ethyleneglycol itoconate, or combinations thereof.

5. The process of claim 1 wherein the vicinal functional oligomer is a polystearyl methacrylate vicinal diol, and the isocyanate is a polyisocyanate.

6. The process of claim 1 wherein the polymer microspheres are spherical and have a particle size between about 0.01 microns and about 500 microns.

7. The process of claim 1 wherein the polymer microspheres encapsulate a solid or liquid active ingredient.

8. The process of claim 7 wherein the active ingredient comprises, benzisothiazolinone, quaternary ammonium salts, epoxy oligomers, acrylic oligomers, isocyanate oligomers, 2,4-dichlorophenoxyacetic acid, sulfentrazone, or combinations thereof.

9. The process of claim 1 wherein the monomer is styrene.

\* \* \* \* \*